United States Patent [19]
Booren

[11] Patent Number: 4,822,611
[45] Date of Patent: Apr. 18, 1989

[54] ORAL HYPOSENSITIZATION IN THE TREATMENT OF ALLERGIES

[75] Inventor: Jack C. Booren, Denver, Colo.

[73] Assignee: Immunotec, Inc., San Diego, Calif.

[21] Appl. No.: 939,949

[22] Filed: Dec. 9, 1986

[51] Int. Cl.$^4$ .................... A61K 35/78; A61K 31/70
[52] U.S. Cl. ................................. 424/195.1; 514/23; 514/826; 514/885
[58] Field of Search .............. 424/195.1; 514/23, 826, 514/885

[56] References Cited
PUBLICATIONS

Cooper et al: A Controlled Trial of Oral Hyposensitization in Pollen Asthma and Rhinitis in Children. *Clin. Allergy*, 14, 541–550 (1984).

Taudorf et al: Oral Administration of Grass Pollen to Hay Fever Patients. *Allergy*, 40, 321–335 (1985).

Björkstén, et al: Clinical and Immunological Effects of Oral Immunotherapy with a Standardized Birch Pollen Extract. *Allergy*, 41, 290–295 (1986).

Möller et al: Oral Immunotherapy of Children with Rhinoconjunctivitis Due to Birch Pollen Allergy. *Allergy*, 41, 271–279 (1986).

*Primary Examiner*—John W. Rollins, Jr.
*Attorney, Agent, or Firm*—Sherman Gilbert Davis

[57] ABSTRACT

A method of treating allergies whereby hyposensitization to allergens to which the patient has been found to be sensitive by skin testing and history is induced by sequentially scheduled oral administration of titrated amounts of allergenic extracts in a liquid vehicle comprising defined proportions of a selected hexose monosaccharide and ethyl alcohol in water.

4 Claims, No Drawings

ORAL HYPOSENSITIZATION IN THE TREATMENT OF ALLERGIES

BACKGROUND OF THE INVENTION

This invention relates to the treatment of allergies, and more specifically to immunotherapy by administration of allergenic extracts by the oral route as an alternative to injection therapy.

Unusual susceptibility or hypersensitivity in humans to any offending substance is commonly termed an "allergy", and the offending substance is termed an "allergen". Concentrated solutions of allergens used for diagnosis or treatment of allergic disease are known as "allergenic extracts".

Types of allergy have been divided into four subdivisions based on type of reaction. The simplest reaction, called a Type I or anaphylactic reaction, is the category into which most cases of simple allergy fall. These cases include seasonal rhinitis or hay fever, stinging insect bite, some food and drug allergies, extrinsic bronchial asthma, and some cases of urticaria. The present invention relates to this type of allergy.

A Type I reaction is mediated by a group of antibodies known as "reagins" or skin-sensitizing antibodies, and these are designated by the symbol IgE. Reagin may circulate in the serum or bind to certain cells. When antigen in the form of an allergen reacts with this cell-bound reagin, certain substances, among them histamine, are believed to be released, and the familiar allergic or atopic reaction occurs.

Immunotherapy has been a mainstay in the treatment of hypersensitivity for many years. Long before the true nature of Type I, IgE mediated hypersensitivity was elucidated, immunotherapy was accepted by the medical community as a means for ameliorating allergic symptoms.

The mechanism for relief of allergy symptoms with this form of treatment is not entirely clear. It has been shown that there is both a reduction of allergen-specific IgE antibody levels to the administered allergen with time, as well as a rise in specific IgG, the so-called bocking antibody. The decreased IgE level reduces the patient's "sensitivity", possibly through the activation of suppressor T-cell activity, which inhibits specific IgE release from plasma cells. The enhanced IgG level appears to prevent coating of the mast cell surface by IgE, thus blocking receptor sites of the IgE molecules and inhibiting the events that would lead to release of chemical mediators of local allergic symptoms.

Formerly referred to as "desensitization", but currently more correctly referred to as "hyposensitization", immunotherapy has been used for the remediation of allergic symtoms resulting from all classes of allergens such as inhalants, injectants, contactants and ingestants.

Most commonly, allergic immunotherapy is employed in cases in which a patient has a history suggesting an allergic condition, and has a significantly positive allergy skin test to one or more specific allergens. Treatment involves the injection of graduated doses of the specific allergenic extracts to which the patient has been found to be sensitive, followed by maintenance doses of the highest concentrations of extracts tolerated by the patient that relieves symptoms without producing undesirable local or general reactions. The size of this dose and the interval between doses can be adjusted as necessary. The interval between doses may in some instances be increased from one week or less to as long as four weeks, but protection is usually lost rapidly if the interval is more than four weeks, At least a 50 percent reduction in symptoms should be expected in most patients after one to two years of immunotherapy with an extract of the specific allergen or allergens.

As with any injection of a foreign substance, or antigen, there is always a risk of local reaction, and occasionally systemic reactions to these biologically potent materials may occur. In certain individuals, systemic reactions may be life-threatening. Accordingly, caution must be used in determining the rate of dosage increase, and patients should be carefully observed following injection treatment.

Extensive literature over the past several decades confirms the utility of hyposensitization by hypodermic injection of allergenic extracts in the treatment of specific allergies. However, despite improvements in quality of the extracts and reduction in the number and severity of side-effects, the treatment is still very demanding on both patient and doctor, requiring many visits, 20 to 30 minutes observation after each injection, and continued risk of systemic reactions. Treatment has also been more effective for certain classes of allergens than for others, which may be an attribute of the route of administration.

Oral immunotherapy as an alternative to injection therapy may, under the proper conditions, provide a treatment which is at least equally as effective, while eliminating some of the negative and often traumatic aspects of injection therapy. Published papers have shown minimum side-effects and few systemic reactions from this form of treatment, even when doses of allergen or allergenic extracts significantly higher than those used for injection therapy were administered. Treatment was done entirely in the home, as is common with other oral medication. Patients did not miss school or work, and transportation expenses for professional administration were minimized. The traumatic aspects of hypodermic injections, particularly with children, were likewise eliminated. Effective oral immunotherapy could, therefore, represent an inexpensive and safe form of allergy treatment which my also broaden the range of effectiveness.

DESCRIPTION OF THE PRIOR ART

Oral hyposensitization has been evaluated in the treatment of allergic diseases by a number of clinicians, particularly in cases of rhinoconjunctivitis and asthma from pollen allergies, and the method has been relatively widely used, especially in southern Europe. However, most of the studies claiming a beneficial effect from oral hyposensitization were open and uncontrolled, and reported beneficial effects have been subject to question.

Several investigators have claimed that oral immunotherapy has been effective in the treatment of patients allergic to certain pollens, but in controlled trials, symptomatic differences between placebo and actively treated patients did not prove to be statistically significant. It was suggested that this lack of proveable effect could possibly be explained by low potency of the extracts used, and by partial digestion of the allergen in the stomach and duodenum. Subsequent studies in which higher doses of allergenic extracts were employed in a form which allowed the allergen to reach the small intestine have shown statistically significant effects.

Cooper, et al: A controlled trial of oral hyposensitization in pollen asthma and rhinitis in children. *Clin. Allergy*, 14, 541–550 (1984) reported a study on the effect of an orally administered grass pollen vaccine, taken preseasonally, on the clinical symptoms of children with hay fever, asthma or both during grass pollen season. An aqueous solution containing a mixture of twelve grass pollens preserved in phenol was used for one group. Placebo consisting of phenol-saline solution was used for the other group. The treatment schedule involved administration of gradually increasing numbers of drops of grass pollen solutions of increasing concentrations on a daily basis to a maximum, after which this maximum dosage was administered as a maintenance dose twice weekly. Symptoms were rated on diary cards showing number of days on which symptoms were present and severity of symptoms.

None of the symptomatic differences between control and actively treated patients were statistically significant, although actively treated patients did show some positive response. The investigators concluded that this study failed to show a significant advantage for active treatment over placebo, suggesting that the vaccine had at best small effect.

Taudorf, et al: Oral administration of grass pollen to hay fever patients. *Allergy*, 40, 321–335 (1985) reported a double-blind placebo efficacy study of oral hyposensitization. Clinically, this was the first placebo-controlled study using in vitro standardized enterosoluble grass pollen tablets for oral hyposensitization in hay fever, and involved a higher dosage than had previously been employed in similar studies.

The study failed to prove any beneficial effect from oral hyposensitization measured by symptom score, medication score, nasal provocation test or skin prick test. There was no change in specific IgE and IgG which could be attributed to the treatment, and no beneficial effect was found despite a very high dosage schedule.

Notable in this paper was a discussion of the origin and mechanics of production of specific antibodies. Of particular interest was the observation that there is substantial evidence that the precursors of IgA-producing plasma cells in salivary and lacrimal glands originate from gut-associated lymphoid tissues and mesenteric lymph nodes, and thus evidence that ingestion of particulate antigen may cause specific antibody formation in external secretions. Accordingly, oral therapy for inhaled antigens should be more effective than injection therapy because of elicitation of secretory IgA which is extruded into the linings of the lungs, bronchi, and bronchioles. This secretory IgA represents a first line of defense by blocking the inhaled antigen from ever reaching the cells of the reticuloendothelial system.

Also of note was the observation by the investigators that although their study of the efficacy of oral hyposensitization using enterosoluble grass pollen tablets failed to show any treatment effect, oral hyposensitization of allergies might later prove successful. They suggested that it "may only be a question of increasing the dose of allergens, adding adjuvants to the allergen powder, or increasing the medication period, or perhaps ensuring delivery of active allergen to a specific, as yet unknown, site in the gastrointestinal tract".

A study by Björksten, et al: Clinical and immunological effects of oral immunotherapy with a standardized birch pollen extract. *Allergy*, 41, 290–295 (1986), was designed to further evaluate oral immunotherapy in the light of published findings. This study employed high doses of a defined freeze-dried birch pollen extract administered in enteric coated gelatin capsules to overcome lack of effect due to possible low potency of extracts or partial digestion of the allergen in the stomach or duodenum. Patients whose allergy to birch pollen had previously been evaluated were from two geographically separate centers, and actively treated patients were maintained on their maximum tolerated level of extract under two different regimens. All of the actively treated patients in both groups showed significantly reduced symptom scores compared with controls following treatment. Side effects, particularly from the gastrointestinal tract, appeared in all treated patients, and a systemic reaction occurred with one patient.

The investigators concluded that oral immunotherapy may be effective, provided that high doses of a defined allergen preparation are used, and that the immune system in the intestinal mucosa is reached and stimulated.

Successful treatment by oral immunotherapy was reported by Möller, et al: Oral immunotherapy of children with rhinoconjunctivitis due to birch pollen allergy. *Allergy*, 41, 271–279 (1986). This study was conducted by many of the same investigators involved in the previously cited report by Bjorksten, et al, and had as its objectives to eliminate side-effects through a modification of the treatment, to confirm that oral immunotherapy is an effective form of treatment, and to study in more detail the immune responses during oral immunotherapy.

Patients were treated with enteric coated capsules containing either a birch pollen preparation or placebo. Birch pollen preparation in the capsules provided a weekly dose up to 80 times greater than that used for subcutaneous immunotherapy.

Compared with the placebo group, the actively treated group had lower symptom scores, significantly decreased skin reactions, increased levels of IgE and IgG antibodies against birch before the birch pollen season, and suppression of the seasonal increase in levels of IgE antibodies against birch. Conjunctival sensitivity was lower in the active group than in the placebo group after 3 months of treatment, but not after 10 months.

No general reactions occurred, and side effects consisted of only minor gastrointestinal disturbances in 80 percent of the treated patients. These symptoms were also noted in some of the placebo patients, but in a much lower percentage.

The investigators concluded that this study confirmed and extended the findings of their previous study that oral administration of high doses of allergen extracts in entericcoated capsules represents a potentially valuable tool for immunotherapy and showed that side effects could be reduced by proper dose schedules.

SUMMARY OF THE INVENTION

The object of the present invention is to provide a means for hyposensitization treatment of allergies employing a liquid vehicle to which allergens or allergenic extracts may be conveniently added in amounts effective for ameliorating allergic symptoms, and which will allow these allergens to reach the reticuloendothelial system in their immunogenic form when administered by the oral route, with minimal side effects or reactions.

The oral administration of an allergenic extract present certain problems which are not encountered in hypodermic administration, as for example, the enzymatic and acidic degradation of the antigen by components of the gastrointestinal tract. Heretofore, liquid vehicles have not been found to be effective in transporting allergens to the reticuloendothelial system by this route.

In the gastrointestinal tract, there are three locations where lymphoid cells of the reticuloendothelial system are encountered, namely the tonsils, the Peyer's patches at the terminal end of the small intestine, and the appendix. While a minor activation of the reticuloendothelial system may be stimulated at the tonsillar level, it is generally believed that the major activating site lies in the Peyer's patches. Accordingly, the antigen must reach this site intact.

Most commonly, protection of an orally administered drug or therapeutic from absorption or destruction before it reaches a particular location in the gastrointestinal tract has been achieved by enteric coating of a tablet or capsule, for example, or by some form of delayed release structure or coating.

Formulations for delayed release have also been made by enteric coating pellets or granules, and these coated particles may be dispersed in a liquid. Under these conditions, however, the particles still react as solids in the stomach and intestine.

Since the active component or components of an enteric coated dosage form will not be released until the dosage form passes into the intestinal tract, gastric emptying time becomes an important factor. Studies of the gastric emptying of pharmaceutical solids indicate that tablets or capsules may be retained in the stomach from a few minutes to as long as twelve hours. Liquids, on the other hand, appear to empty continuously at a more predictable, possibly exponential, rate. Under these circumstances, a liquid vehicle which could protect allergen extracts during rapid passage through the stomach could be expected to provide uniform and predictable delivery of active components to the site of action in the small intestine. The liquid vehicle of the present invention appears to function in this manner.

Liquid preparations for oral delivery of drugs and other therapeutics have been long known and used in pharmacy in the form of plain aqueous solutions, syrups, suspensions, and elixirs, for example, but such vehicles heretofore employed in oral allergic sensitzation studies have been found to be of limited efficacy.

Syrups traditionally are concentrated solutions of sugar, usually sucrose. In addition to sucrose, other sugars, and certain polyols such as sorbitol or glycerin, to inhibit crystallization and to modify solubilization, taste, mouth-feel and other properties, may be added. Syrups may contain a small concentration of alcohol as a preservative or as a solvent to incorporate flavors or the medicament itself. Glucose has been added to syrups of acid reaction, in some instances, to minimize discoloration of levulose produced by inversion of sucrose, or where the reducing action of glucose may prevent oxidative change. Alcohol content in some syrup preparations may range from around 2 to around 5 percent, and glucose may be present up to around 10 percent.

Elixirs are clear, sweetened, hydroalcoholic liquids intended for oral use. Glucose may be present in some medicated elixirs, for example, as part of a syrup included for sweetening or flavor. Alcohol in elixirs may range from around 8 percent to as high as around 80 percent. Glucose would generally not exceed 8 to 10 percent.

Wine is occasionally used as a vehicle, and in pharmacy generally refers to grape wines. These wines normally contain up to 14 percent alcohol by volume, and the principal sugar is glucose. Wines, particularly red wines, are considered unsuitable for use in allergy therppy because of histamine reactions.

Alcohol and Dextrose Injection, U.S.P., contains ethyl alcohol and dextrose in sterile water. This preparation normally contains 5 to 10 percent of alcohol, and 5 percent of dextrose, and is administered parenterally as a source of carbohydrate calories that restore blood glucose levels.

Dextrose, or glucose, and levulose, or fructose, are the only monosaccharides which occur in nature in the free state to any important extent. They are present in the juices of many ripe fruits. Dextrose contains an aldehyde function and a total of 6 carbon atoms and is, therefore, classified as an "aldohexose" monosaccharide. Similarly, fructose contains a ketone function and a total of 6 carbon atoms and is classified as a "ketohexose" monosaccharide. The aldohexose sugars are of most interest in this invention. This class of monosaccharides includes Allose, Talose, Gulose, Mannose, Glucose, Idose, Galactose and Altrose.

DESCRIPTION OF THE INVENTION

According to this invention, hyposensitization to various allergens is induced by sequentially scheduled oral administrtion of titrated amounts of the allergens to which the patient has been found to be sensitive, in a liquid vehicle comprising defined proportions of a selected hexose monosaccharide and ethyl alcohol in water.

In studies evaluating various vehicles, it was determined that water alone, water and alcohol mixtures, and solutions of various concentrations of disaccharide and monosaccharide sugars either individually or in combination in water alone were not effective, but that solutions containing certain hexose monosaccharides together with ethyl alcohol in water were able to provide effective transport for the allergen extracts.

The preferred vehicle comprises:

a selected hexose monosaccharide, from 4.5 to 5.5 percent by weight;

ethyl alcohol, from 13.5 to 16.5 percent by volume in distilled water.

Components should be of highest chemical purity. Distilled water or water purified to meet the requirements for Water for Injection, U.S.P., are preferred.

Best results were obtained with the aldohexose monosaccharide sugars, of which dextrose and galactose are the preferred members in this invention. Both are normally found in the body, and are available commercially and used in other pharmaceutical applications and products.

Biochemically, ethanol is converted in the body to acetaldehyde, which causes a shift in the redox potential and may affect enzymatic activity. This could slow the degradation of the antigen as it passes through the alimentary tract. At the same time, free glucose or galactose are preferentially absorbed by the cells of the villi lining the small intestine, galactose being even more readily absorbed than glucose. This could facilitate passage of the allergen with minimum degradation until it is picked up by the macrophages in the Peyer's patches. Such conditions together with the rapid gastric emptying of the liquid could contribute to the unexpected results observed with the use of this vehicle.

PREPARATION OF THE VEHICLE

In practice, the vehicle may be prepared according to the following non-limiting examples, which illustrate the preparation procedure:

EXAMPLE 1

To 1500 ml. of distilled water, in a suitable container equipped with a mixer or blender, is added 100 grams of Dextrose Anhydrous, U.S.P., allowing it to mix to complete dissolution, followed by 300 ml. of Dehydrated Alcohol, U.S.P., and additional water in sufficient quantity to make a final volume of 2000 ml. Mixing is continued to assure complete dispersion of the components, and the solution is transferred to suitable containers for dispensing.

EXAMPLE 2

To 1500 ml. of water meeting the requirements for Water for Injection, U.S.P., in a suitable container equipped with a mixer or blender, is added 110 grams of Dextrose (D-Glucose monohydrate) U.S.P., allowing it to mix to complete dissolution, followed by 316 ml. of Alcohol, U.S.P. (ethyl alcohol, 95% by volume) and additional water in sufficient quantity to make a final volume of 2000 ml. Mixing is continued to complete dispersion of the components, and the solution is transferred to suitable containers for dispensing.

EXAMPLE 3

To 1500 ml. of distilled water, in a suitable container equipped with a mixer or blender, is added 110 grams of galactose monohydrate, allowing it to mix to complete dissolution, followed by 316 ml. of Alcohol, U.S.P., (ethyl alcohol, 95% by volume) and additional water in sufficient quantity to make a final volume of 2000 ml. Mixing is continued to assure complete dispersion of the components, and the solution is transferred to suitable containers for dispensing.

It is obvious from these examples that a variety of other methods for determining quantities of components and combining them can be employed in the preparation of the vehicle. It is likewise obvious that other processing steps may be employed, and various non-allergenic pharmaceutical necessities such as stabilizers and preservatives may be incorporated in the composition for commercial manufacture and packaging of the vehicle.

PREPARATION OF ALLERGEN SOLUTIONS

Allergenic extract solutions for oral administration in the practice of this invention are prepared according to the specific needs of the patient as determined by conventional skin testing procedures and confirming history and symptomatology. The same commercially available "bulk" allergenic extracts used in the preparation of solutions for hyposensitization by hypodermic injection are effective for oral use according to this invention as well, and the same precautions with respect to handling, batch to batch variation, and differences in extracts from different manufacturers must be observed. Concentrations of allergens in the solutions for administration, as well as potencies of individual doses, may differ significantly, however.

Among the advantages of practice of allergic hyposensitization according to the present invention is that measurement of the administered doses need not be as precise as that required for subcutaneous injection. For example, dosage may be measured in drops rather than in precise fractions of a milliliter in a hypodermic syringe. This is of considerable importance, since attendance by a physician or other trained professional is not necessary for administration, and daily dose measurements can be done by the patient or other non-professional with minimal instruction.

Typically, an oral allergenic extract preparation for a given patient may be prepared according to the following non-limiting illustrative example:

As determined by tests, volumes of 0.2 ml. of a 1:10 weight to volume dilution of commercially available bulk extracts of each of the allergens to which the patient has been found to be sensitive are transferred to a 2 ounce dropper bottle and thoroughly mixed with prepared vehicle to make up a total volume of 60 ml. This solution is dispensed to the patient, with appropriate directions for use as with any other orally administered prescription.

Individual doses are taken by the patient, diluted preferably in one to two ounces of cold water or fruit juice, according to the following schedule:
Day 1: 1 drop, AM; 1 drop, PM;
Day 2: 2 drops, AM; 2 drops, PM;
Day 3: 3 drops, AM; 3 drops, PM;
Day 4: 4 drops, AM; 4 drops, PM;
Day 5: 5 drops, AM; 5 drops, PM
adding one drop to the daily individual doses until satisfactory symptomatic response is achieved. The determined dosage is continued as the daily maintenance dose, administered twice a day for the duration of treatment.

The dropper used for measurement should meet the requirements of the Pharmacopeial medicine dropper which, when held vertically, delivers water in drops each of which weighs between 45 mg. and 55 mg., or nominally 0.05 ml.

Those skilled in the art will recognize that this procedure allows for significant flexibility in adjustment of concentration of allergen extract in the dispensed solution and volume of individual doses by the physician, and overcomes many of the drawbacks of hypodermic injection therapy and previous oral therapy procedures.

It should be particularly noted that the dosage according to this invention is based on satisfactory symptomatic response only, since significant local or general reactions have not been observed at dosage levels providing the desired response. The comparative safety and absence of reactions to oral immunotherapy may possibly be attributed to the fact that when an allergen is injected, a variety of cells are activated, including macrophages, B-cells, T-cells, and mast cells. The mast cells, as noted previously, release the chemical mediators of allergic reactions. With effective oral administration of allergen, only the macrophages are stimulated, with subsequent stimulation or activation of cells of the immune system.

The invention may be variously otherwise embodied within the scope of the appended claims.

I claim:

1. A method of treating allergy in humans by hyposensitization to allergens to which the patient has been found to be sensitive comprising sequentially scheduled oral administration of titrated amounts of allergenic extracts in a prepared liquid vehicle comprising defined proportions of a selected hexose monosaccharide and ethyl alcohol in water until a level providing satisfactory symptomatic response is achieved, and continued administration of this dosage for the duration of treatment.

2. A method according to claim 1, wherein the vehicle comprises:

a selected hexose monosaccharide, from 4.5 to 5.5 percent by weight;

ethyl alcohol, from 13.5 to 16.5 percent by volume, in distilled water.

3. A method according to claim 2, wherein the hexose monosaccharide is an aldohexose monosaccharide.

4. A method according to claim 3, wherein the aldohexose monosaccharide is selected from the group consisting of dextrose and galactose.

* * * * *